(12) United States Patent
Siddique et al.

(10) Patent No.: US 11,801,317 B2
(45) Date of Patent: Oct. 31, 2023

(54) SURFACE COATING CONFIGURED TO ENHANCE UV STERILIZATION AND METHOD OF MANUFACTURING THE SAME

(71) Applicant: Samsung Electronics Co., Ltd., Suwon-si (KR)

(72) Inventors: Radwanul Hasan Siddique, Pasadena, CA (US); Yibing Michelle Wang, Temple City, CA (US)

(73) Assignee: Samsung Electronics Co., Ltd., Yongin-si (KR)

(*) Notice: Subject to any disclaimer, the term of this patent is extended or adjusted under 35 U.S.C. 154(b) by 336 days.

(21) Appl. No.: 17/036,452

(22) Filed: Sep. 29, 2020

(65) Prior Publication Data

US 2021/0299294 A1    Sep. 30, 2021

Related U.S. Application Data

(60) Provisional application No. 63/036,638, filed on Jun. 9, 2020, provisional application No. 63/001,243, filed on Mar. 27, 2020.

(51) Int. Cl.
*G02B 1/10* (2015.01)
*B05D 1/00* (2006.01)
(Continued)

(52) U.S. Cl.
CPC ............ *A61L 2/087* (2013.01); *A61L 2/10* (2013.01); *G02B 1/10* (2013.01); *B05D 1/60* (2013.01); *G02B 2207/101* (2013.01)

(58) Field of Classification Search
CPC ....... B05D 1/60; G02B 2207/101; G02B 1/10
See application file for complete search history.

(56) References Cited

U.S. PATENT DOCUMENTS

| 8,137,523 B2 | 3/2012 | Cho et al. |
| 10,199,415 B2 | 2/2019 | Akselrod et al. |

(Continued)

FOREIGN PATENT DOCUMENTS

| CN | 106395569 A | | 2/2017 |
| DE | 10201311440 | * | 9/2017 |

(Continued)

OTHER PUBLICATIONS

Escoubas, Ludovic, et al., "Design and realization of light absorbers using plasmonic nanoparticles," Progress in Quantum Electronics, vol. 63, 2019, pp. 1-22.

(Continued)

*Primary Examiner* — Elizabeth A Burkhart
(74) *Attorney, Agent, or Firm* — Lewis Roca Rothgerber Christie LLP

(57) ABSTRACT

A surface coating configured to locally enhance ultraviolet light density of ultraviolet light incident on the surface coating. The surface coating includes a dielectric layer, a conductive layer on the dielectric layer, a series of nano-openings in the dielectric layer and the conductive layer, a series of nano-antennae in the series of nano-openings, and a dielectric gap between the series of nano-antennas and the conductive layer. The conductive layer and the nano-antennae both include a UV plasmonic material.

20 Claims, 9 Drawing Sheets
(1 of 9 Drawing Sheet(s) Filed in Color)

(51) Int. Cl.
*A61L 2/08* (2006.01)
*A61L 2/10* (2006.01)

(56) References Cited

U.S. PATENT DOCUMENTS

| | | | |
|---|---|---|---|
| 10,571,606 B2* | 2/2020 | Altug | G01N 21/658 |
| 2008/0187457 A1 | 8/2008 | Mangiardi | |
| 2014/0358128 A1* | 12/2014 | Montazeri | G02B 6/12002 |
| | | | 604/890.1 |
| 2019/0298483 A1 | 10/2019 | Estermann et al. | |
| 2021/0009819 A1 | 1/2021 | Zweig | |

FOREIGN PATENT DOCUMENTS

| EP | 3581624 A1 | 12/2019 |
|---|---|---|
| KR | 10-2108889 B1 | 5/2020 |

OTHER PUBLICATIONS

EPO Extended European Search Report dated Sep. 24, 2021, issued in corresponding European Patent Application No. 21160749.4 (9 pages).

* cited by examiner

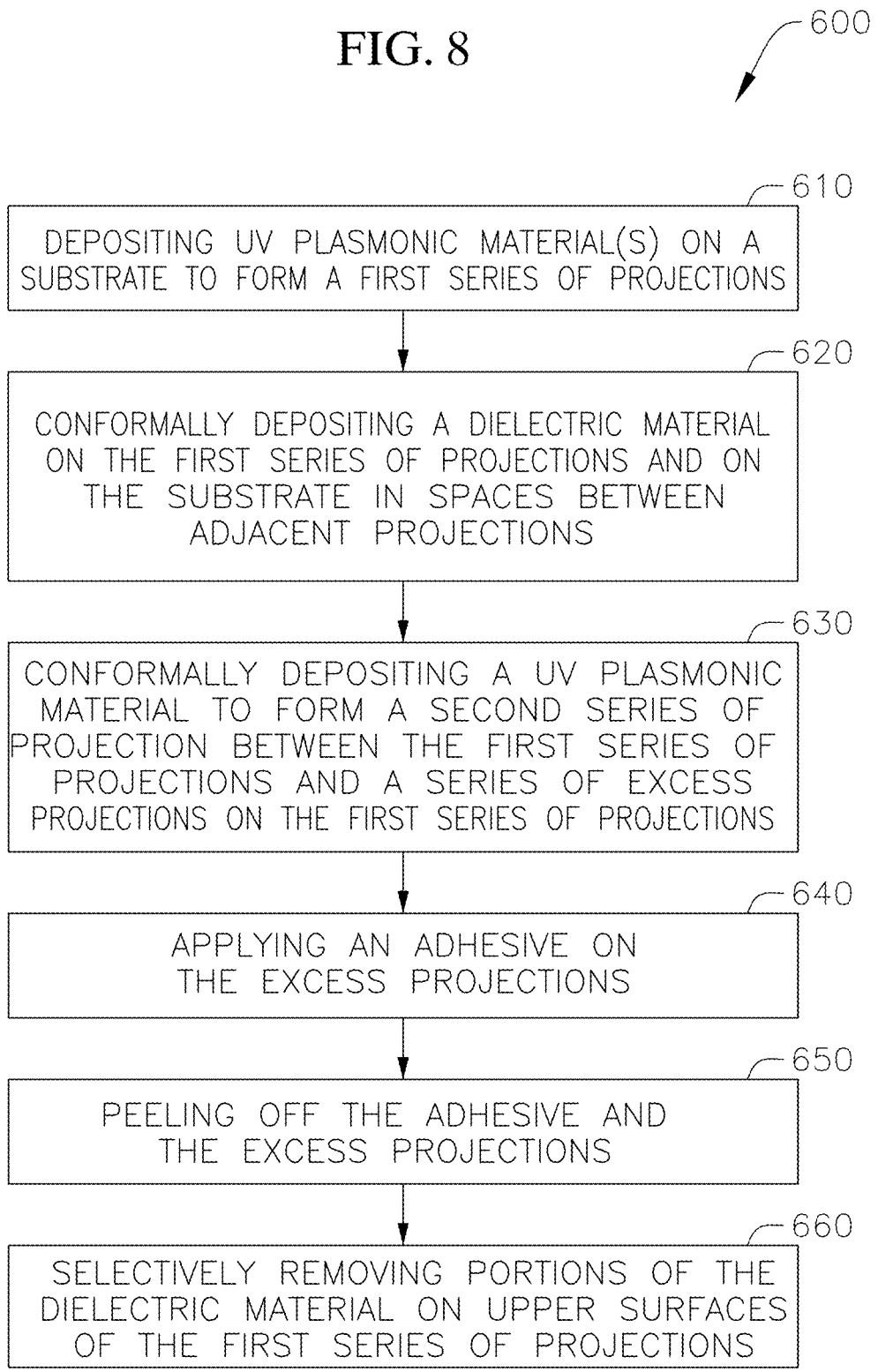

SURFACE COATING CONFIGURED TO ENHANCE UV STERILIZATION AND METHOD OF MANUFACTURING THE SAME

CROSS-REFERENCE TO RELATED APPLICATION(S)

The present application claims priority to and the benefit of U.S. Provisional Application No. 63/036,638, filed Jun. 9, 2020, the entire content of which is incorporated herein by reference. The present application also claims priority to and the benefit of U.S. Provisional Application No. 63/001,243, filed Mar. 27, 2020.

BACKGROUND

1. Field

The present application relates generally to surface coatings configured to enhance UV sterilization and methods of manufacturing said surface coatings.

2. Description of Related Art

Ultraviolet (UV) light (200-320 nm) is commonly used to sterilize surfaces against viral and microbial pathogens. UV light sterilizes surfaces by destroying the genetic material inside viruses and other microbes. Moreover, UVC light (200-280 nm), which a specific band of UV light, is widely used for disinfection. For instance, UVC lamps and robots are commonly used to sanitize water and air purifiers, cleaning objects such as laboratory equipment, and spaces such as buses and airplanes. UVB light (280-320 nm) can be used as disinfection too, but UVB light requires either high dosage or longer exposure time compared to UVC light for effective disinfection. Typical dosages for effective disinfection are greater than 60 mJ/cm$^2$ for UVC light, and greater than 1000 mJ/cm$^2$ for UVB light.

However, exposure to UVC light is more dangerous for people than exposure to UVB light, and existing UVC sanitizers are not safe for human exposure. Per the EU Health agency guidelines, human exposure to UVC light is safe at a dosage of 3 mJ/cm$^2$ or less for a maximum of 8 hours per day. Exposure to UVC light at higher dosages and/or for a longer duration can damage human eyes and skin, and can cause cancer.

SUMMARY

The present application relates to various embodiments of a surface coating configured to locally enhance ultraviolet light density of ultraviolet light incident on the surface coating. In one embodiment, the surface coating includes a dielectric layer, a conductive layer on the dielectric layer, a series of nano-openings in the dielectric layer and the conductive layer, a series of nano-antennae in the series of nano-openings, and a series of dielectric gaps between the series of nano-antennas and the conductive layer. The conductive layer and the series of nano-antennae both include a UV plasmonic material.

The dielectric gap of the series of dielectric gaps has a distance of approximately 10 nm or less.

The UV plasmonic material may be aluminum (Al), gallium (Ga), indium (In), tin (Sn), thallium (Tl), lead (Pb), bismuth (Bi), magnesium (Mg), germanium (Ge), gallium nitride (GaN), or a combination thereof.

The dielectric layer may include polymethyl methacrylate (PMMA), silica (SiO$_2$), or a low-index dielectric material.

Each nano-antenna of the series of nano-antennae may have a circular shape, a spherical shape, an ellipsoidal shape, a prismatic shape (e.g., square or rectangular shape), or a tapered shape.

An average diameter of the series of nano-antennae may be in a range from approximately 20 nm to approximately 500 nm.

At least one nano-antenna of the series of nano-antennae may have a shape or size different than another nano-antenna of the series of nano-antennae.

A periodicity of the series of nano-antennae may be in a range from approximately 50 nm to approximately 1,000 nm.

The series of nano-openings and the series of nano-antennae may be provided over at least 60% of the surface coating.

A surface coating according to another embodiment of the present disclosure includes a layer of UV plasmonic material including a series of nano-antennae, and a dielectric pattern in the layer of UV plasmonic material. The dielectric pattern spaces adjacent nano-antennae of the series of nano-antennae apart from each other by a dielectric gap.

The dielectric gap may have a distance of approximately 10 nm or less.

The UV plasmonic material may be aluminum (Al), gallium (Ga), indium (In), tin (Sn), thallium (Tl), lead (Pb), bismuth (Bi), magnesium (Mg), germanium (Ge), gallium nitride (GaN), or a combination thereof.

The dielectric pattern may include an array of shapes, grid lines, stripes, chevrons, a sawtooth pattern, a crisscross pattern, or a combination thereof.

An average width of the series of nano-antennae may be in a range from approximately 20 nm to approximately 500 nm.

The present disclosure also relates to various methods of manufacturing a surface coating. In one embodiment, the method includes depositing a mixture of a first polymer and a second polymer on a substrate, wherein the second polymer self-arranges into a series of spots. The method also includes selectively removing the series of spots to form a series of nano-openings in the dielectric layer formed by the first polymer, and depositing a UV plasmonic material on the dielectric layer and in the series of nano-openings. The UV plasmonic material forms a series of nano-antennae in the series of nano-openings and a conductive layer on the dielectric layer.

Depositing the mixture may include brushing, spraying, dipping, vapor deposition, or printing.

Depositing the UV plasmonic material may include e-beam evaporation, radio frequency (RF) sputtering, thermal sputtering, or molecular beam deposition of the UV plasmonic material.

The first polymer may include polymethyl methacrylate (PMMA) and the second polymer may include polystyrene (PS).

According to another embodiment of the present disclosure, the method depositing a UV plasmonic material on a substrate to form a first series of projections on the substrate, wherein the first series of projections are spaced apart from each other by spaces. The method also includes depositing a dielectric material on the first series of projections and in the spaces between the first series of projections, depositing a UV plasmonic material to form a second series of projections in the spaces between the first series of projections and a series of excess projections on the first series of projections, removing the series of excess projections, and selectively removing portions of the dielectric material on the first series of projections, The first series of projections and the second series of projections define nano-antennae of the conductive layer, and remaining portions of the dielectric material define a dielectric pattern.

Removing the series of excess projections may include applying an adhesive on the series of excess projections, and peeling off the adhesive and the series of excess projections adhered thereto.

The present disclosure also relates to various embodiments of a method of sterilizing a surface includes a series of nano-antennae and a series of dielectric gaps. In one embodiment, the method includes irradiating the surface with ultraviolet light having a first dosage safe for human exposure from an ultraviolet light source. During the irradiating the surface with the ultraviolet light, the series of dielectric gaps locally increases the first dosage of the ultraviolet light to a second dosage higher than the first dosage, wherein the second dosage is unsafe for human exposure.

The second dosage may be at least approximately 1,000 times greater than the first dosage.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features may be combined with one or more other described features to provide a workable device.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale. Additionally, the patent or application file contains at least one drawing executed in color. Copies of this patent or patent application publication with color drawing(s) will be provided by the Office upon request and payment of the necessary fee.

FIG. 8 is a flowchart illustrating tasks of a method of manufacturing the embodiment of the surface coating illustrated in FIGS. 7A-7B according to one embodiment of the present disclosure;

DETAILED DESCRIPTION

Figures 1A, 1B:
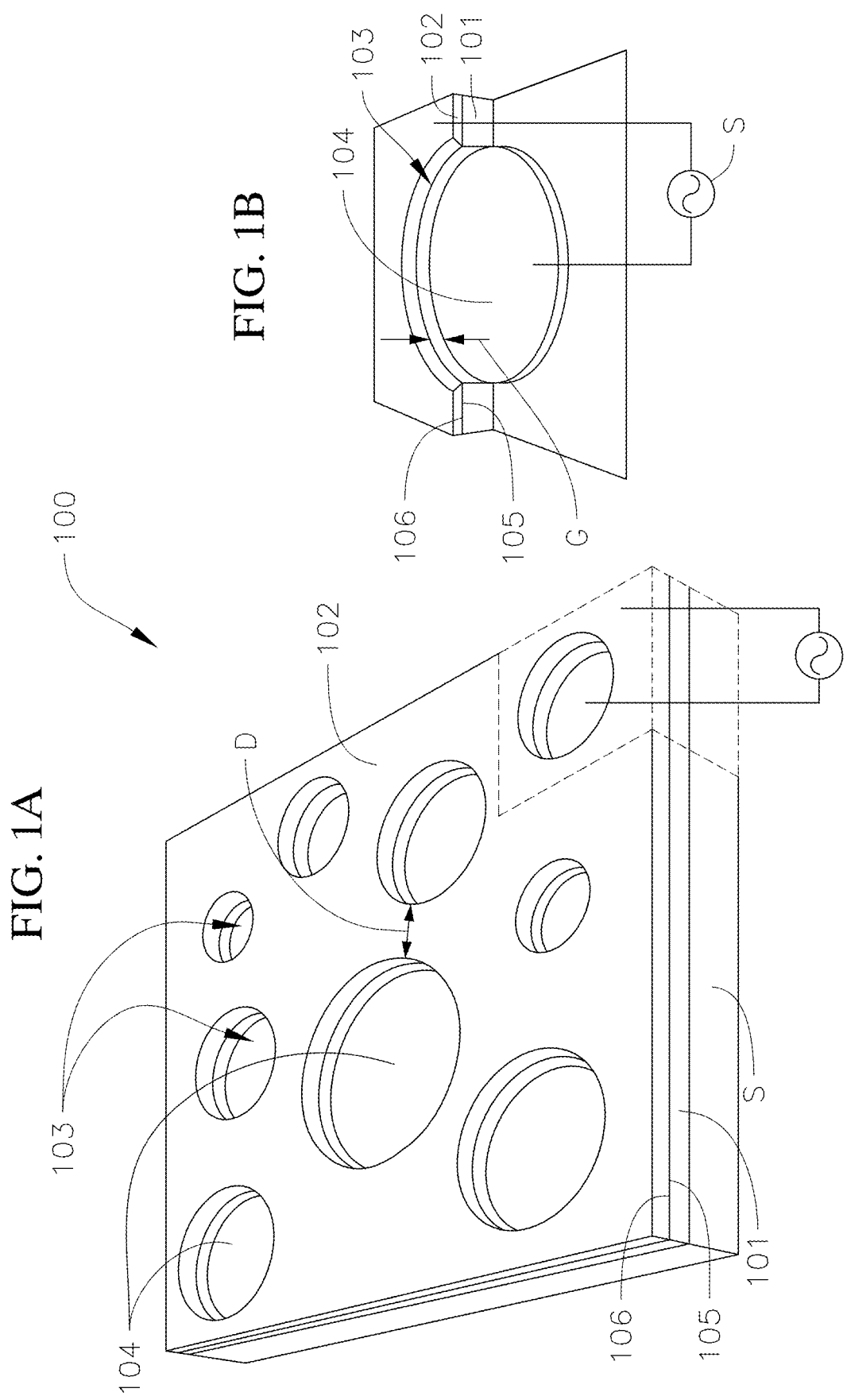
FIGS. 1A-1B are a perspective view and a detail cutaway view, respectively, of a surface coating including a series of nanoantennae according to one embodiment of the present disclosure.

The present application relates to various embodiments of a surface coating, and a method of making a surface coating, that is configured to locally enhance ultraviolet (UV) light density when the surface coating is irradiated with a UV light source. In one or more embodiments, the surface coating includes an array of nano-antennae that have a single resonance or broadband resonances at target UV light source wavelengths. Accordingly, the surface coating may be irradiated with an ultra-low power dosage of UV light within safe human limits, and the surface coating may locally increase the density of the UV light and the local electromagnetic field to effectively kill microbial and viral pathogens on the surface coating and to accelerate the disinfection rate for high-throughput performance. That is, the nano-antennae are configured to spatially confine incident UV light to increase the effective dosage of the incident UV light. Additionally, in one or more embodiments, the surface coating is configured to scatter UV light incident on the surface coating over a wide range of angles (e.g., the surface coating exhibits omni-directional light enhancement properties), which increases light-matter interactions to kill pathogens on the surface coating effectively.

Hereinafter, example embodiments will be described in more detail with reference to the accompanying drawings, in which like reference numbers refer to like elements throughout. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof may not be repeated.

In the drawings, the relative sizes of elements, layers, and regions may be exaggerated and/or simplified for clarity. Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present invention.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the term "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

FIGS. 1A-1B depict a surface coating 100 according to one embodiment of the present disclosure. The surface coating 100 may be applied to a substrate S of any suitable article or fixture that is desired to be sterilized against microbial and viral pathogens (e.g., air-conditioning filtration systems, high-touch surfaces such as elevator buttons, doorknobs, and door handles, and/or any other surface that is likely to contribute to the transmission of pathogens). In the illustrated embodiment, the surface coating 100 includes a dielectric layer 101, a conductive layer 102 on the dielectric layer 101, a series of nano-openings 103 (e.g., nano-holes or nano-cavities) extending through the conductive layer 102 and the dielectric layer 101, and a series of nano-antennas 104 in the nano-openings 103. In the illustrated embodiment, the nano-antennas 104 are recessed in the nano-openings 103. Additionally, in the illustrated embodiment, each of the nano-antennas 104 are recessed in the nano-openings 103 below an interface between an upper surface 105 of the dielectric layer 101 and a lower surface 106 of the conductive layer 102. Accordingly, in the illustrated embodiment, the nano-antennas 104 are spaced apart from the conductive layer 102 by a portion of the dielectric layer 101 (i.e., the nano-antennas 104 are spaced apart from the conductive layer 102 by a dielectric gap G). In one or more embodiments, the dielectric gap G between the nano-antennas 104 and the conductive layer 102 may be approximately 10 nm or less (i.e., in the illustrated embodiment, the nano-antennas 104 are recessed in the nano-openings 103 such that the distance between the upper surface 105 of each of the nano-antennas 104 and the lower surface 106 of the conductive layer 102 along the dielectric layer 101 is approximately 10 nm or less). In one or more embodiments, the dielectric gap G between the nano-antennas 104 and the conductive layer 102 may be approximately 5 nm or less.

The conductive layer 102 and the nano-antennae 104 may be formed of any UV plasmonic material or combination of UV plasmonic materials, such as a metal (e.g., aluminum (Al), gallium (Ga), indium (In), tin (Sn), thallium (Tl), lead (Pb), bismuth (Bi), and/or magnesium (Mg)) or a metalloid (e.g., germanium (Ge)). In one or more embodiments, the conductive layer 102 and the nano-antennae 104 may be formed of gallium nitride (GaN) or aluminum nitride (AlN).

Additionally, in the illustrated embodiment, the nano-openings 103 and the nano-antennas 104 therein are circular, and the nano-openings 103 and the nano-antennas 104 have a diameter in a range from approximately 20 nm to approximately 500 nm. In one or more embodiments, the nano-openings 103 and the nano-antennas 104 may have any other suitable shape, such as, for example, any tapered shaped (e.g., an oval shape, an elliptical shape, or a spherical shape) or a prismatic shape (e.g., square or rectangular shape).

In the illustrated embodiment, the nano-antennas 104 may be spaced apart from adjacent nano-antennas 104 by a distance D in a range from approximately 50 nm to approximately 1,000 nm (e.g., the array of nano-antennas 104 may have a periodicity in a range from approximately 50 nm to approximately 1,000 nm). In one or more embodiments, the nano-openings 103 and the corresponding nano-antennas 104 may be provided along any suitable portion of the surface coating 100, such as, for example, approximately 60% or more of the surface coating 100.

In use, when UV light (e.g., UVC and/or UVB light) is incident on the surface coating 100, coupling between the photons in the incident UV light and the free electrons on the surfaces of the conductive layer 102 and the nano-antennae 104 (i.e., the free electrons in the UV plasmonic material(s)) flow toward the dielectric gaps G (i.e., the free electrons flow toward the dielectric interfaces between the conductive layer 102 and the nano-antennae 104). The dielectric gaps G between the conductive layer 102 and the nano-antennae 104 restrict the flow of free electrons between the conductive layer 102 and the nano-antennae 104, which creates a build-up of the electrons at the dielectric gaps G. This build-up of electrons traps the electric field in the dielectric gaps G and thereby locally increases the electromagnetic field intensity at the dielectric gaps G. That is, when UV light is incident on the surface coating 100, the free electrons in the UV plasmonic material of the nano-antennae 104 flow radially outward toward the dielectric gaps G, and the free electrons in the UV plasmonic material of the conductive layer 102 flow towards the edges of the nano-openings 103, which traps the electric field in the dielectric gaps G and locally increases the electromagnetic field strength at the dielectric gaps G due to a capacitive-like effect. In general, reducing the size of the dielectric gap G between the nano-antennae 104 and the conductive layer 102 increases the local enhancement of the electromagnetic field intensity at the dielectric gaps G. For example, in one or more embodiments, the dielectric gaps G between the nano-antennae 104 and the conductive layer 102 are configured to locally increase the effective dosage of the UV light incident on the surface coating 100 by a factor greater than approximately 1,000. In one or more embodiments, the dielectric gaps G between the nano-antennae 104 and the conductive layer 102 are configured to locally increase the effective dosage of the UV light incident on the surface coating 100 by a factor in a range from approximately 500 to approximately 1,500 or more.

Figure 2:
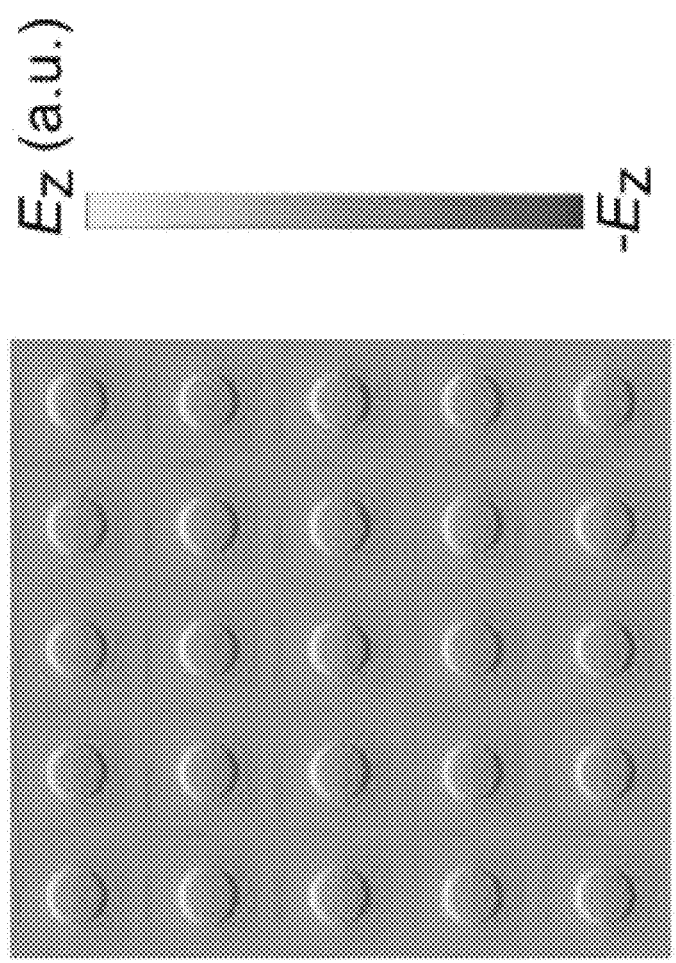
FIG. 2 is a color plot depicting the local electromagnetic field strength at the nanoantennae according to one embodiment of the present disclosure.
Figure 3:
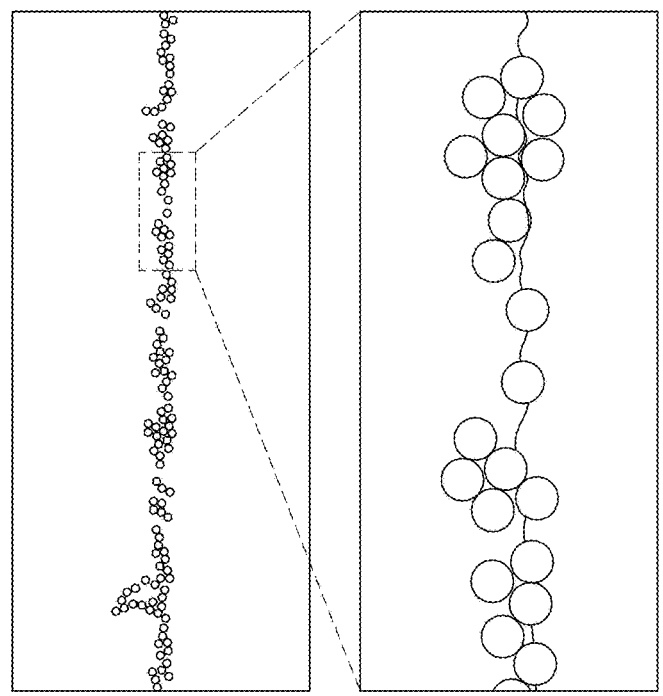
FIG. 3 depicts scanning electron microscope (SEM) photographs showing viral and/or other microbial pathogens drawn to a dielectric gap due to dielectricphoresis (DEP)
Figure 4:
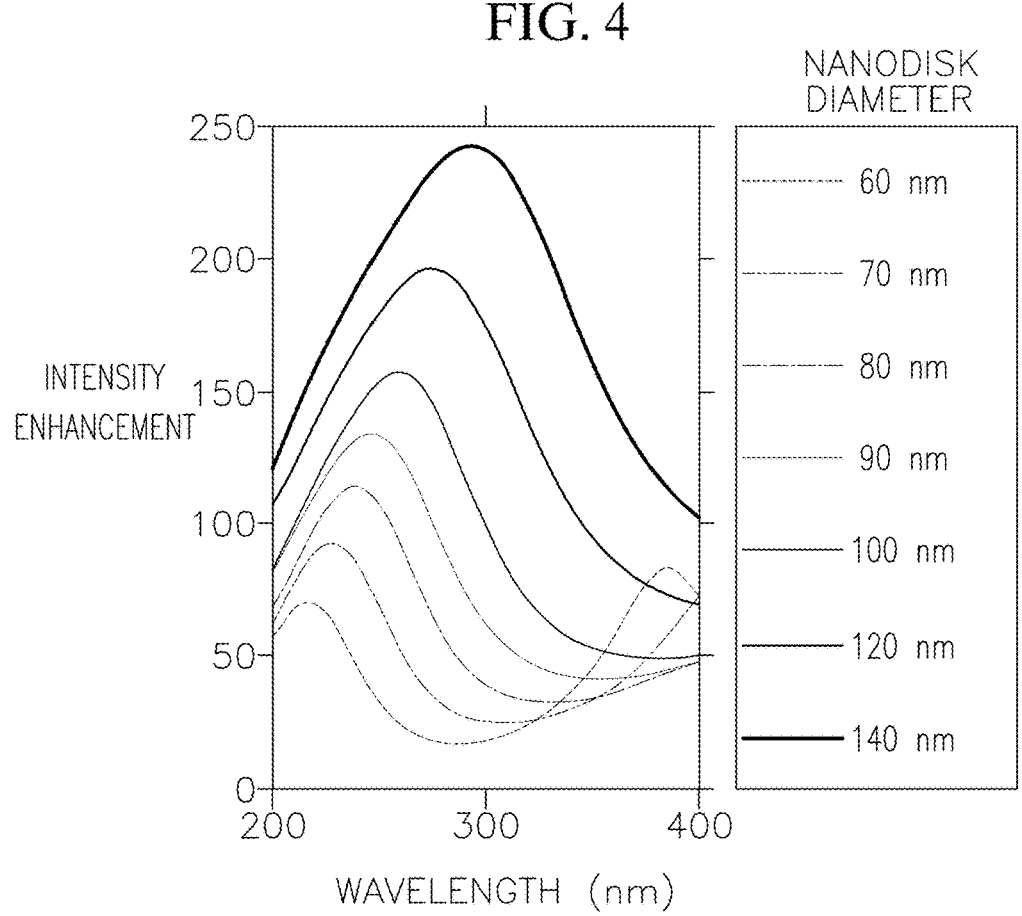
FIG. 4 is a graph depicting the local intensity enhancement factor of the surface coating as a function of the diameter of the nano-antennae for incident UV light having a frequency in a range from 200 nm to 400 nm.

FIG. 2 is a color plot depicting the local electromagnetic field strength (E) at the nano-antennae 104 of the surface coating 100 according to one embodiment of the present disclosure. In FIG. 2, the portions of the nano-antennae 104 shown in yellow exhibit a relatively higher local electromagnetic field strength, and the portions of the nano-antennae 104 shown in blue exhibit a relatively lower local electromagnetic field strength. As illustrated in FIG. 2, when the UV light source utilized to irradiate the surface coating is UVC light having a frequency of approximately 250 nm and a dose of approximately 1 mJ/cm$^2$, the maximum local effective dose of the UV light at the dielectric gaps G between the nano-antennae 104 and the conductive layer 102 of the surface coating 100 is increased to approximately 1,334 mJ/cm$^2$ (i.e., the dielectric gaps G between the nano-antennae 104 and the conductive layer 102 of the surface coating 100 are configured to locally increase the effective dosage (the electromagnetic density) of the UV light incident on the surface coating 100 by a factor of more than 1,000). Accordingly, in one or more embodiments, a dosage of UV light safe for human exposure but not sufficient to destroy viruses or other microbial pathogens (e.g., UVC light having a dosage of approximately 3 mJ/cm$^2$ or less) may be directed toward the surface coating 100, and the intensity of the UV light may be locally enhanced at the dielectric gaps G to a dosage sufficient to destroy the genetic material inside the virus and/or other microbes on the surface coating 100.

Additionally, in one or more embodiments, viral pathogens and/or microbial pathogens on the surface coating 100 may be electrically drawn to dielectric gaps G between the nano-antennas 104 and the conductive layer 102 (e.g., viral pathogens and/or microbial pathogens may be drawn toward and electrically trapped in the dielectric gaps G) due to the phenomenon of dielectricphoresis (DEP). FIG. 3 depicts scanning electron microscope (SEM) photographs showing viral and/or other microbial pathogens drawn to a dielectric gap due to DEP. DEP is a phenomenon in which a force is exerted on a dielectric particle, such as viral and microbial pathogens, when it is subjected to a non-uniform electric field. This force does not require the particle to be charged. All particles exhibit DEP activity in the presence of electric fields. In the embodiment illustrated in FIGS. 1A-1B, an alternating current (AC) source is applied to the nano-antennas 104 and the conductive layer 102 across the dielectric gaps G formed by the dielectric layer 101. Accordingly, when the AC source is applied to the nano-antennas 104 and the conductive layer 102, the viral and/or microbial pathogens are electrically drawn and confined by DEP to the dielectric gaps G. Electrically drawing the viral and/or microbial pathogens to the dielectric gaps G is configured to increase the exposure of the viral and/or microbial pathogens to the UV light that is trapped and enhanced at the dielectric gaps G. In this manner, applying an AC source to the nano-antennas 104 and the conductive layer 102 across the dielectric gaps G is configured to enable the incident UV light to destroy viruses and/or other microbial pathogens located on portions of the surface coating 100 that do not enhance the dosage of the incident light and that therefore might not otherwise be destroyed.

The configuration (e.g., shape and size) of the nano-antennae 104 may be selected such that each nano-antenna 104 has a single resonance or two or more resonances (e.g., broadband resonances) at the wavelengths of the UV light source that will be utilized to sterilize the surface coating 100. At resonant wavelengths, each nano-antenna 104 of the surface coating 100 is configured to spatially confine incident UV light to increase the effective dosage of the UV light (i.e., the nano-antennae 104 of the surface coating 100 are configured to effectively increase the local electromagnetic density of the UV light incident on the surface coating 100). In general, different viruses or other microbial pathogens are vulnerable to genetic destruction by different wavelengths of light. Accordingly, if the wavelength of the incident UV light is selected to destroy the genetic material of a particular virus or other microbial pathogen, then the diameters of the nano-antennae 104 (or the mean diameter of the Gaussian distribution of diameters) may be selected such the nano-antennae 104 exhibit resonance at that selected frequency of incident UV light.

FIG. 4 is a graph depicting the local intensity enhancement factor of the surface coating 100 as a function of the diameter of the nano-antennae 104 for incident UV light having a frequency in a range from 200 nm to 400 nm. As illustrated in FIG. 4, nano-antennae 104 having a diameter of approximately 140 nm exhibit resonance at a wavelength of approximately 295 nm, nano-antennae 104 having a diameter of approximately 120 nm exhibit resonance at a wavelength of approximately 280 nm, nano-antennae 104 having a diameter of approximately 100 nm exhibit resonance at a wavelength of approximately 260 nm, nano-antennae 104 having a diameter of approximately 90 nm exhibit resonance at a wavelength of approximately 250 nm, nano-antennae 104 having a diameter of approximately 80 nm exhibit resonance at a wavelength of approximately 240 nm, nano-antennae 104 having a diameter of approximately 70 nm exhibit resonance at a wavelength of approximately 230 nm, and nano-antennae 104 having a diameter of approximately 60 nm exhibit resonance at a wavelength of approximately 220 nm. As described above, in one or more embodiments, the diameter of the nano-antennae 104 (or the mean diameter of the Gaussian distribution of diameters) may be selected such the nano-antennae 104 exhibit resonance at the frequency of incident UV light. Even though the intensity enhancement factor of the nano-antennae 104 exhibiting resonance for a particular wavelength may be less than the intensity enhancement factor of nano-antennae 104 that are off resonance at that particular wavelength (e.g., at a wavelength of approximately 250 nm, nano-antennae 104 having a diameter of approximately 90 nm exhibit a resonance intensity enhancement factor of approximately 130 and nano-antennae 104 having a diameter of 140 nm exhibit an off-resonance intensity enhancement factor of approximately 225), it may be beneficial to select the diameter of the nano-antennae 104 such that the nano-antennae 104 exhibit resonance because this will result in the highest confinement of the UV light at the dielectric gaps G.

In one or more embodiments, the surface coating 100 may include nano-antennae 104 having two or more different configurations (e.g., two or shapes and/or two or more different sizes) depending, for instance, on the wavelengths of the UV light source that will be utilized to sterilize the surface coating 100 and to increase the bandwidth of the resonances of the nano-antennae 104. Moreover, as described above, in one or more embodiments, the diameters of the nano-antennae 104 have a Gaussian distribution. Accordingly, in one or more embodiments, the nano-antennae 104 exhibit resonance at a variety of different wavelengths. Thus, broadband UV light (e.g., sunlight), rather than UV light having a wavelength targeted at a specific virus or other microbial pathogen, may be utilized because different nano-antennae 104 are configured to exhibit resonance at different wavelengths of the incident light.

Figure 5:
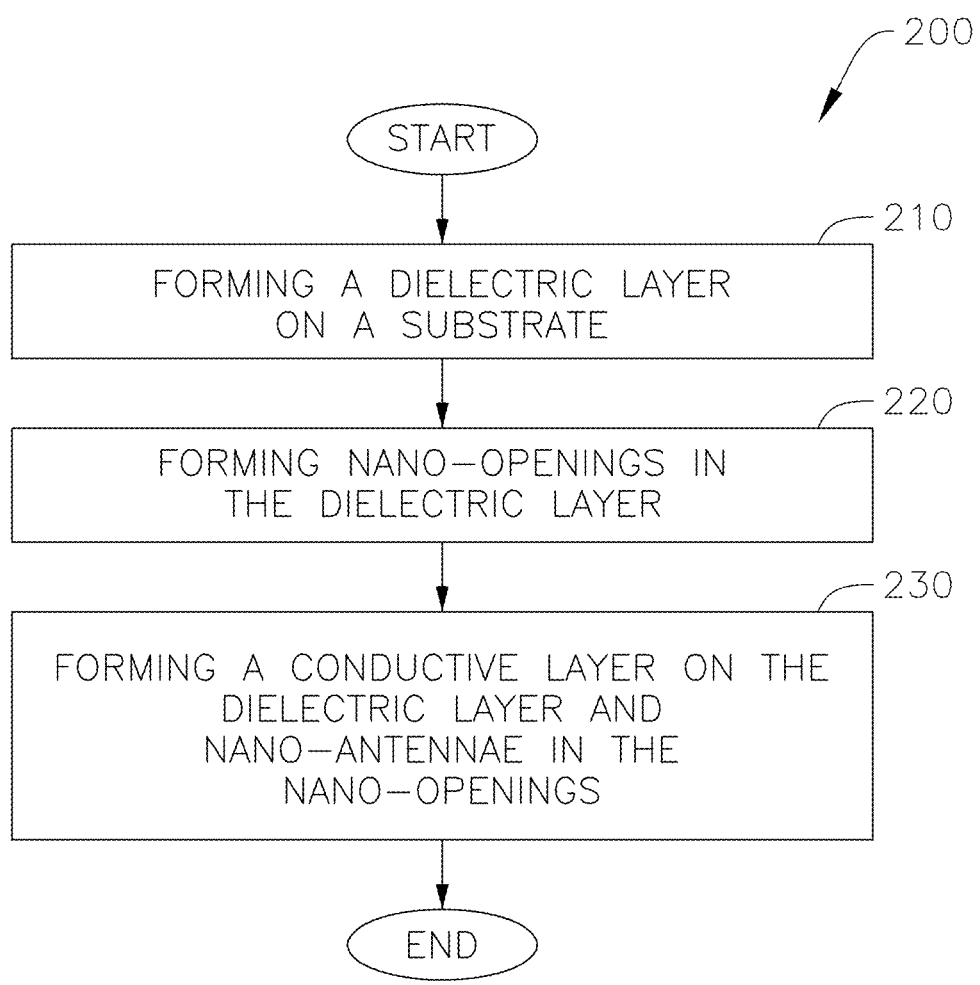
FIG. 5 is a flowchart illustrating tasks of a method of manufacturing the embodiment of the surface coating illustrated in FIGS. 1A-1B according to one embodiment of the present disclosure.
Figure 6A:
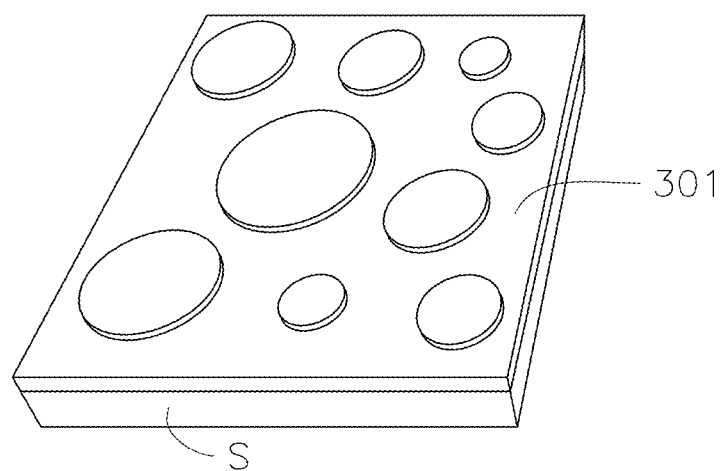
FIGS. 6A-6C are perspective views illustrating the tasks of manufacturing the surface coating according to the method illustrated in FIG. 5.
Figure 6B:
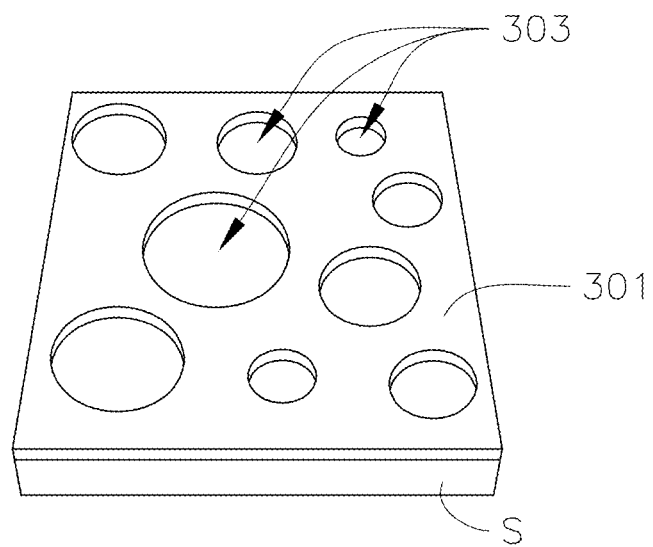
Figure 6C:
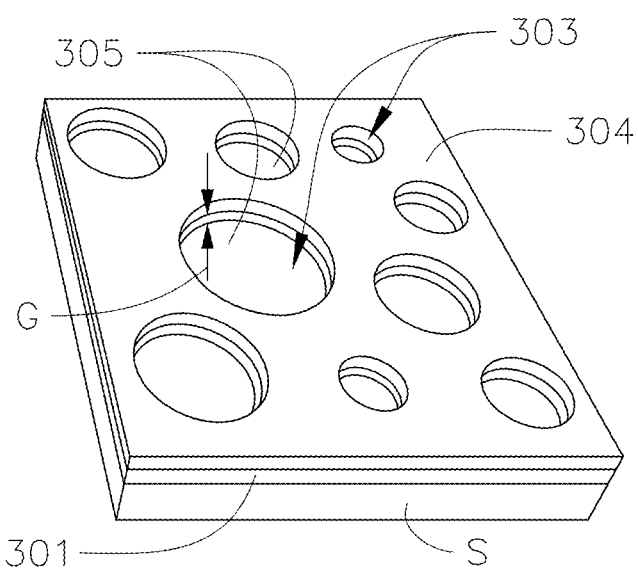

FIG. 5 is a flowchart illustrating tasks of a method 200 of manufacturing the embodiment of the surface coating 100 illustrated in FIGS. 1A-1B and applying the surface coating 100 to an article or a fixture according to one embodiment of the present disclosure. FIGS. 6A-6C are perspective views of the tasks of the method 200 of manufacturing the surface coating 100.

In the embodiment illustrated in FIGS. 5 and 6A, the method 200 includes a task 210 of forming a dielectric layer on a substrate of the article or the fixture. In one embodiment, the task 210 of forming the dielectric layer includes mixing two polymers 301, 302 (e.g., polymethyl methacrylate (PMMA) 301 and polystyrene (PS) 302) together in a solution (e.g., a solvent, such as cyclohexanone), and applying this mixture onto the substrate S of the article or the fixture. The task 210 of applying the mixture of polymers 301, 302 on the substrate S may be performed in any suitable manner, such as, for example, brushing, spraying, dipping, vapor deposition, or printing. Additionally, during task 210, the mixture of the two polymers 301, 302 may be deposited with any suitable thickness on the substrate S depending on the desired thickness of the dielectric layer and the desired dielectric gap G between the nano-antennae and the conductive layer, as described above. In one or more embodiments, the mixture of the two polymers 301, 302 may be deposited on the substrate S with a thickness in a range from approximately 5 nm to approximately nm. Following the task 210 of depositing the mixture of the two polymers 301, 302 on the substrate S, the first polymer 301 (e.g., the PMMA) defines the dielectric layer.

In the illustrated embodiment, the PS 302 in the mixture is configured to self-assemble into a series of spots (e.g., discs). In a subsequent task of the method 200, the PS spots 302 are utilized to form nano-openings 303 in the dielectric layer. Accordingly, the configuration (e.g., shape and size) of the PS spots 302 define the configuration (e.g., the shape and size) of the nano-openings 303 in the dielectric layer and the configuration (e.g., the shape and size) of the nano-antennae formed in the nano-openings 303. In one or more embodiments, the PS spots 302 have a variety of different diameters having a Gaussian distribution around a median diameter. In one or more embodiments, the median diameter of the PS spots 302 may be a function of a variety of parameters, including, for example, the deposition rate (e.g., spin coating rate), the relative humidity of the chamber in which the mixture of PMMA 301 and PS 302 was deposited, and the ratio of PS 302 to PMMA 301 in the mixture. Accordingly, in one or more embodiments, the task 210 of forming the dielectric layer may include controlling these parameters to achieve the desired diameter (or mean diameter) of the nano-openings and the nano-antennae formed therein. As described above, in one or more embodiments, the diameter (or mean diameter) of the nano-antennae may be selected depending on the wavelength of the incident UV light that will be utilized to destroy viruses and/or other microbial pathogens on the surface coating (e.g., the task 210 may include controlling the deposition rate, the relative humidity of the deposition chamber, and the ratio of PS to PMMA in the mixture such that the subsequently formed nano-antennae exhibit one or more resonance peaks at the wavelength(s) of the incident UV light).

In the illustrated embodiment, the method 200 also includes a task 220 of forming the nano-openings 303 (e.g., holes) in the dielectric layer to expose portions of the underlying substrate S. In one embodiment, the task 220 of forming the nano-openings 303 in the dielectric layer comprises selectively developing the PS spots 302 to remove the portions of the dielectric layer in contact with the PS spots 302. The task of selectively removing the PS spots 302 may utilize any solvent having a suitable selectivity of the second polymer 302 (e.g., PS) with respect to the first polymer 301 (e.g., PMMA). In one or more embodiments, the task 220 may include rinsing the deposited PS and PMMA mixture 301, 302 twice in cyclohexane for 60 seconds and then drying the deposited PS and PMMA mixture 301, 302 in a stream of nitrogen ($N_2$) to remove the PS spots 302.

In the illustrated embodiment, the method 200 also includes a task 230 of forming a conductive layer 304 on the dielectric layer 301 (e.g., the PMMA layer) and a plurality of nano-antennae 305 in the nano-openings 303 formed in task 220. In the illustrated embodiment, the task 230 of forming the conductive layer 304 and the nano-antennae 305 includes conformally depositing a UV plasmonic material or a combination of UV plasmonic materials on the dielectric layer 301 and in the nano-openings 303 in the dielectric layer 301. In one or more embodiments, the UV plasmonic material(s) deposited in task 230 may be a metal (e.g., aluminum (Al), gallium (Ga), indium (In), tin (Sn), thallium (Tl), lead (Pb), bismuth (Bi), and/or magnesium (Mg)) or a metalloid (e.g., germanium (Ge)). In one or more embodiments, the UV plasmonic material(s) deposited in task 230 may be gallium nitride (GaN) or aluminum nitride (AlN). The task 230 of depositing the UV plasmonic material(s) may be performed in any suitable manner, such as by e-beam evaporation, radio frequency (RF) sputtering, thermal sputtering, or molecular beam deposition. In one or more embodiments, the process utilized to deposit the UV plasmonic material in task 230 may vary depending on the UV plasmonic material(s) selected (e.g., if aluminum is selected as the UV plasmonic material, the process utilized in task 230 may be e-beam evaporation, and if gallium nitride is selected as the UV plasmonic material, the process utilized in task 230 may be molecular beam deposition). Following the task 230 of depositing the UV plasmonic material(s), the UV plasmonic nano-antennae 305 are formed in the nano-openings 303 of the dielectric layer 301 (e.g., the PMMA layer), the UV plasmonic conductive layer 304 is formed on the dielectric layer 301 (e.g., the PMMA layer), and the UV plasmonic nano-antennae 305 are separated from the UV plasmonic conductive layer 304 by dielectric gaps G formed from the dielectric layer 301 (e.g., the PMMA layer).

Figure 7A:
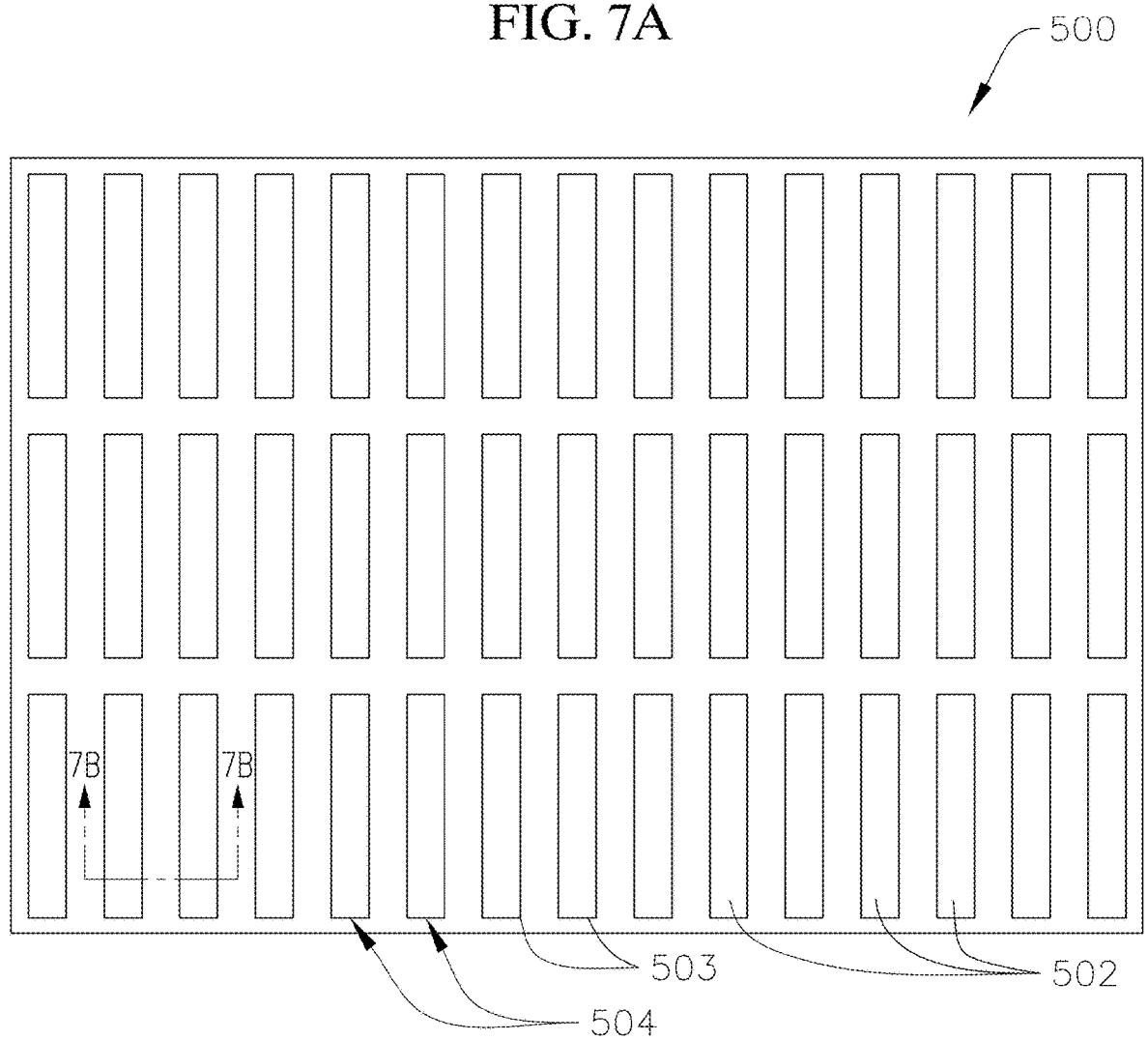
FIGS. 7A-7B are a plan view and a cross-sectional view, respectively, of a surface coating including a series of nano-antennae according to another embodiment of the present disclosure.
Figure 7B:
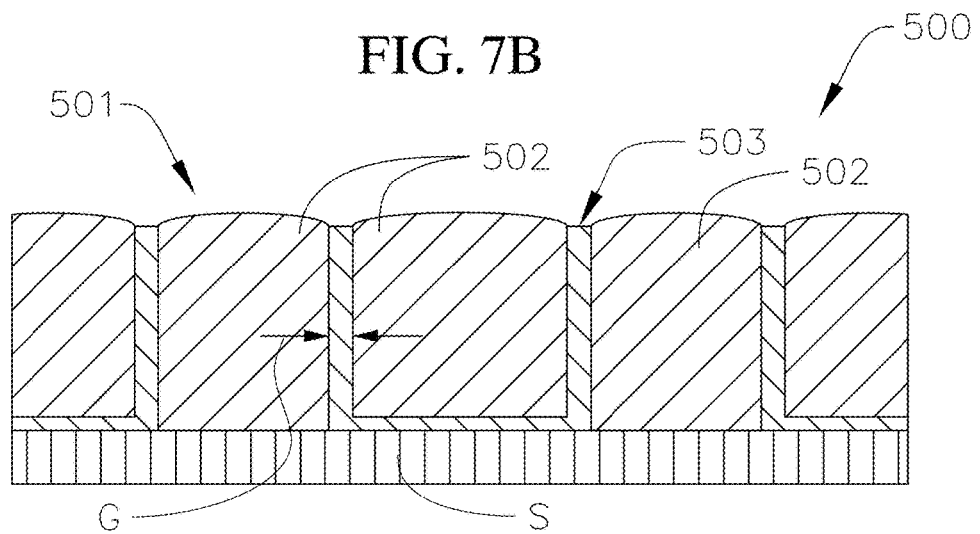

FIGS. 7A-7B depict a surface coating 500 according to one embodiment of the present disclosure. The surface coating 500 may be applied to a substrate S of any suitable article or fixture that is desired to be sterilized against microbial and viral pathogens (e.g., air-conditioning filtration systems, high-touch surfaces such as elevator buttons, doorknobs, and door handles, and/or any other surface that is likely to contribute to the transmission of pathogens). In the illustrated embodiment, the surface coating 500 includes a conductive layer 501 segmented into an array of nano-antennae 502, and a dielectric pattern 503 in the conductive layer 501. The dielectric pattern 503 separate adjacent nano-antennae 502 from each other (i.e., adjacent nano-antennae 502 of the conductive layer 501 are spaced apart by a dielectric gap G formed from the dielectric pattern 503). In one or more embodiments, the dielectric gap G between adjacent nano-antennae 502 of the conductive layer 501 may be approximately 10 nm or less (e.g., approximately 5 nm or less).

In the illustrated embodiment, the dielectric pattern 503 includes an array of discrete rectangular window-frame patterns 504. In one or more embodiments, the dielectric pattern 503 may include an array of other shapes, such as an array of circles, squares, triangles, etc. In one or more embodiments, the dielectric layers 503 may be arranged in any other suitable arrangement or pattern (e.g., grid lines, stripes, chevrons, a sawtooth pattern, or a crisscross pattern). In one or more embodiments, the dielectric pattern 503 may include a series of discrete patterns or a single continuous pattern.

The conductive layer 501 (and the nano-antennae 502 defined thereby) may be formed of any UV plasmonic material or combination of UV plasmonic materials, such as a metal (e.g., aluminum (Al), gallium (Ga), indium (In), tin (Sn), thallium (Tl), lead (Pb), bismuth (Bi), and/or magnesium (Mg)) or a metalloid (e.g., germanium (Ge)). In one or more embodiments, the conductive layer 501 (and the nano-antennae 502 defined thereby) may be formed of gallium nitride (GaN) or aluminum nitride (AlN). The dielectric pattern 503 may be formed of any dielectric material, such as ceramic, glass, or plastic (e.g., polymethyl methacrylate (PMMA)).

In use, when UV light (e.g., UVC and/or UVB light) is incident on the surface coating 500, coupling between the photons in the incident UV light and the free electrons on the surfaces of the nano-antennae 502 (i.e., the free electrons in the UV plasmonic material(s)) flow toward the dielectric gaps G defined by the dielectric pattern 503 (i.e., the free electrons flow toward the dielectric interfaces between adjacent nano-antennae 502). The dielectric gaps G between adjacent nano-antennae 502 restrict the flow of free electrons between the adjacent nano-antennae 502, which creates a build-up of the electrons at the dielectric gaps G. This build-up of electrons traps the electric field in the dielectric gaps G and thereby locally increases the electromagnetic field intensity at the dielectric gaps G. In general, reducing the size of the dielectric gap G between the adjacent nano-antennae 502 increases the local enhancement of the electromagnetic field intensity at the dielectric gaps G. For example, in one or more embodiments, the dielectric gaps G between the adjacent nano-antennae 502 are configured to locally increase the effective dosage of the UV light incident on the surface coating 500 by a factor greater than approximately 1,000. In one or more embodiments, the dielectric gaps G between the adjacent nano-antennae 502 are configured to locally increase the effective dosage of the UV light incident on the surface coating 500 by a factor in a range from approximately 500 to approximately 1,500 or more.

Additionally, in one or more embodiments, viral pathogens and/or microbial pathogens on the surface coating 500 may be electrically drawn to dielectric gaps G between the adjacent nano-antennas 502 of the conductive layer 501 (e.g., viral pathogens and/or microbial pathogens may be drawn toward and electrically trapped in the dielectric gaps G) due to the phenomenon of dielectricphoresis (DEP). In the embodiment illustrated in FIGS. 7A-7B, an alternating current (AC) source is applied to the nano-antennas 502 across the dielectric gaps G formed by the dielectric patter 503. Accordingly, when the AC source is applied to the nano-antennas 502 across the dielectric gaps G, the viral and/or microbial pathogens are electrically drawn and confined by DEP to the dielectric gaps G. Electrically drawing the viral and/or microbial pathogens to the dielectric gaps G is configured to increase the exposure of the viral and/or microbial pathogens to the UV light that is trapped and enhanced at the dielectric gaps G. In this manner, applying an AC source to the nano-antennas 502 across the dielectric gaps G is configured to enable the incident UV light to destroy viruses and/or other microbial pathogens located on portions of the surface coating 500 that do not enhance the dosage of the incident light and that therefore might not otherwise be destroyed.

The configuration (e.g., shape and size) of the nano-antennae 502 may be selected such that each nano-antenna 502 has a single resonance or two or more resonances (e.g., broadband resonances) at the wavelengths of the UV light source that will be utilized to sterilize the surface coating 500. In one or more embodiments, the width of the nano-antennae 502 may be in a range from approximately 20 nm to approximately 500 nm. At resonant wavelengths, each nano-antenna 502 of the surface coating 500 is configured to spatially confine incident UV light to increase the effective dosage of the UV light (i.e., the nano-antennae 502 of the surface coating 500 are configured to effectively increase the local electromagnetic density of the UV light incident on the surface coating 500). In general, different viruses or other microbial pathogens are vulnerable to genetic destruction by different wavelengths of light. Accordingly, if the wavelength of the incident UV light is selected to destroy the genetic material of a particular virus or other microbial pathogen, then the widths of the nano-antennae 502 may be selected such the nano-antennae 502 exhibit resonance at that selected frequency of incident UV light.

FIG. 8 is a flowchart illustrating tasks of a method 600 of manufacturing the embodiment of the surface coating 500 illustrated in FIGS. 7A-7B according to one embodiment of the present disclosure. FIGS. 9A-9E are side views illustrating the surface coating 500 during the method 600 illustrated in FIG. 8.

Figure 9A:
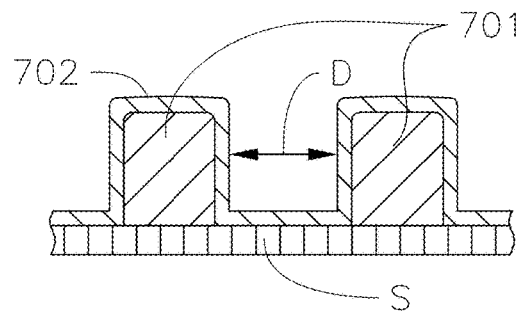
FIGS. 9A-9E are side views illustrating the tasks of manufacturing the surface coating according to the method illustrated in FIG. 8.

In the embodiment illustrated in FIGS. 8 and 9A, the method 600 includes a task 610 of depositing a UV plasmonic material or a combination of UV plasmonic materials on the substrate S. During task 610, the UV plasmonic material forms a first series of projections 701 on the substrate S laterally spaced apart from each other by a distance D. In one or more embodiments, the UV plasmonic material(s) deposited in task 610 may be a metal (e.g., aluminum (Al), gallium (Ga), indium (In), tin (Sn), thallium (Tl), lead (Pb), bismuth (Bi), and/or magnesium (Mg)) or a metalloid (e.g., germanium (Ge)). In one or more embodiments, the UV plasmonic material(s) deposited in task 610 may be gallium nitride (GaN) or aluminum nitride (AlN). The task 610 of depositing the UV plasmonic material(s) may be performed in any suitable manner, such as by e-beam evaporation, radio frequency (RF) sputtering, thermal sputtering or molecular beam deposition. In one or more embodiments, the process utilized to deposit the UV plasmonic material in task 610 may vary depending on the UV plasmonic material(s) selected (e.g., if aluminum is selected as the UV plasmonic material, the process utilized in task 610 may be e-beam evaporation, and if gallium nitride is selected as the UV plasmonic material, the process utilized in task 610 may be molecular beam deposition). In task 610, the UV plasmonic material(s) may be deposited by any suitable process or processes, such as e-beam evaporation, dipping, spraying, spin coating, and/or printing. In task 610, the nano-antennae may be formed in any suitable configuration (e.g., shape, size, and arrangement), such as a series of pillars, rods, and/or ribs. Additionally, in task 610, the spaces between adjacent projections 701 may be formed utilizing a mask and a photoresist (e.g., a positive or negative photoresist). In one or more embodiments, the distance D between adjacent projections 701 may be equal or substantially equal to the desired width of each of the nano-antennae in addition to twice the width of each of the dielectric gaps between the nano-antennae.

In the illustrated embodiment, the method 600 also includes a task 620 of conformally depositing a dielectric material 702 on the first series of projections 701 and on the substrate S in the spaces between adjacent projections 701 formed in task 610. The dielectric material 702 deposited in task 620 may be any suitable dielectric material, such as ceramic, glass, or plastic (e.g., polymethyl methacrylate (PMMA)). In task 620, the dielectric material 702 may be deposited in any suitable process or processes, such as atomic layer deposition (ALD), e-beam evaporation, dipping, spraying, coating, brushing, or printing. In task 620, the dielectric material 702 may be deposited with any suitable thickness, such as a thickness of approximately 10 nm or less (or 5 nm or less) depending on the desired dielectric gap G between adjacent nano-antennae.

Figure 9B:
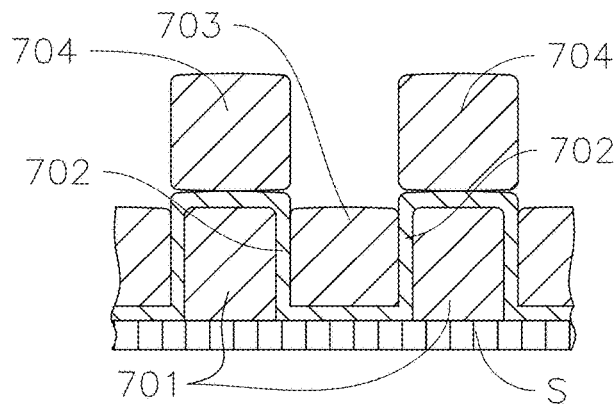

With reference now to the embodiment illustrated in FIGS. 8 and 9B, the method 600 also includes a task 630 of conformally depositing a UV plasmonic material on the dielectric material 702 deposited in task 620. The UV plasmonic material deposited in task 630 forms a second series of projections 703 on the portions of the dielectric material 702 in the spaces between the first series of projections 701, and series of excess projections 704 on the portions of the dielectric material 702 on the first series of projections 701. The UV plasmonic material deposited in task 630 may be the same as the UV plasmonic material deposited in task 610 (e.g., aluminum (Al), gallium (Ga), indium (In), tin (Sn), thallium (Tl), lead (Pb), bismuth (Bi), and/or magnesium (Mg), germanium (Ge), gallium nitride (GaN), and/or aluminum nitride (AlN)) and the UV plasmonic material deposited in task 630 may be deposited in the same manner as the UV plasmonic material deposited in task 610 (e.g., e-beam evaporation or molecular beam deposition).

Figure 9C:
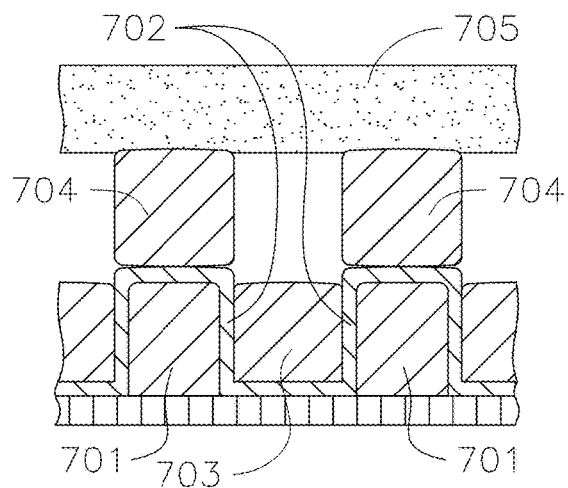

With reference now to the embodiment illustrated in FIGS. 8 and 9C, the method 600 also includes a task 640 of applying an adhesive 705 on the excess projections 704. The adhesive 705 may be any suitable type or kind of adhesive configured to adhere to the UV plasmonic material deposited in task 630.

Figure 9D:
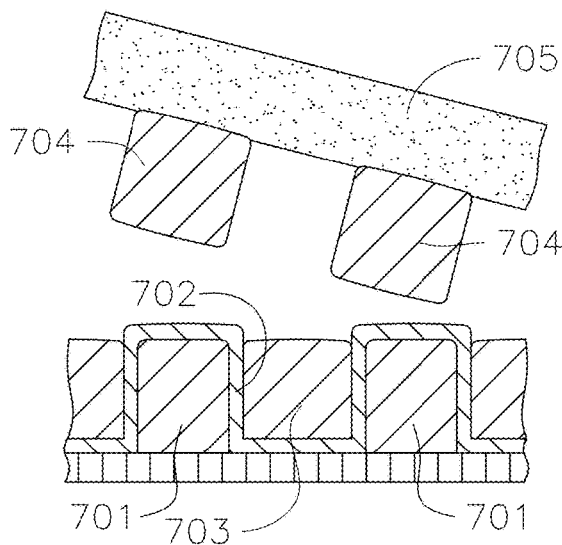

With reference now to the embodiment illustrated in FIGS. 8 and 9D, the method 600 also includes a task 650 of peeling off the adhesive 705 and the excess projections 704 adhered thereto. Following task 650, the excess projections 704 are removed or substantially removed to expose the portions of the dielectric material 702 on the first projections 701. In one or more embodiments, the excess projections 704 may be removed in any other suitable manner, such as by etching.

Figure 9E:
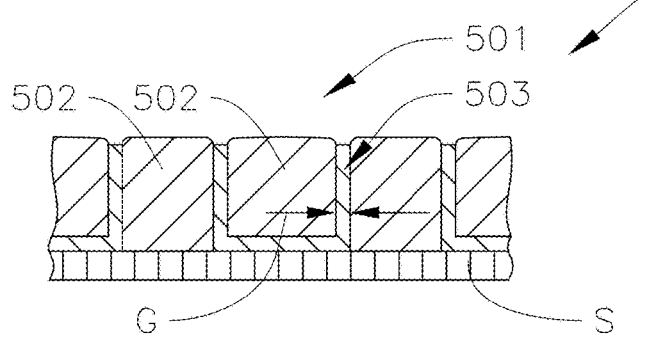

With reference now to the embodiment illustrated in FIGS. 8 and 9E, the method 600 also includes a task 660 of selectively removing the portions of the dielectric material 702 on the upper surfaces of the first series of projections 701. The task 660 of selectively removing the portions of the dielectric material 702 on the first projections 701 may utilize any suitable solvent, such as a solvent having a high selectivity to the dielectric material 702 relative to the UV plasmonic material of the first and second projections 701, 703.

Together, the first projections 701 formed by depositing the UV plasmonic material in task 610 and the second projections 703 formed by depositing the UV plasmonic material deposited in task 630 define the nano-antennae 502 of the conductive layer 501, and the portions of the dielectric material 702 remaining following task 660 define the dielectric pattern 503 and the dielectric gaps G between adjacent nano-antennae 502, as shown in the embodiment of the surface coating 500 illustrated in FIGS. 7A-7B.

Figure 10:
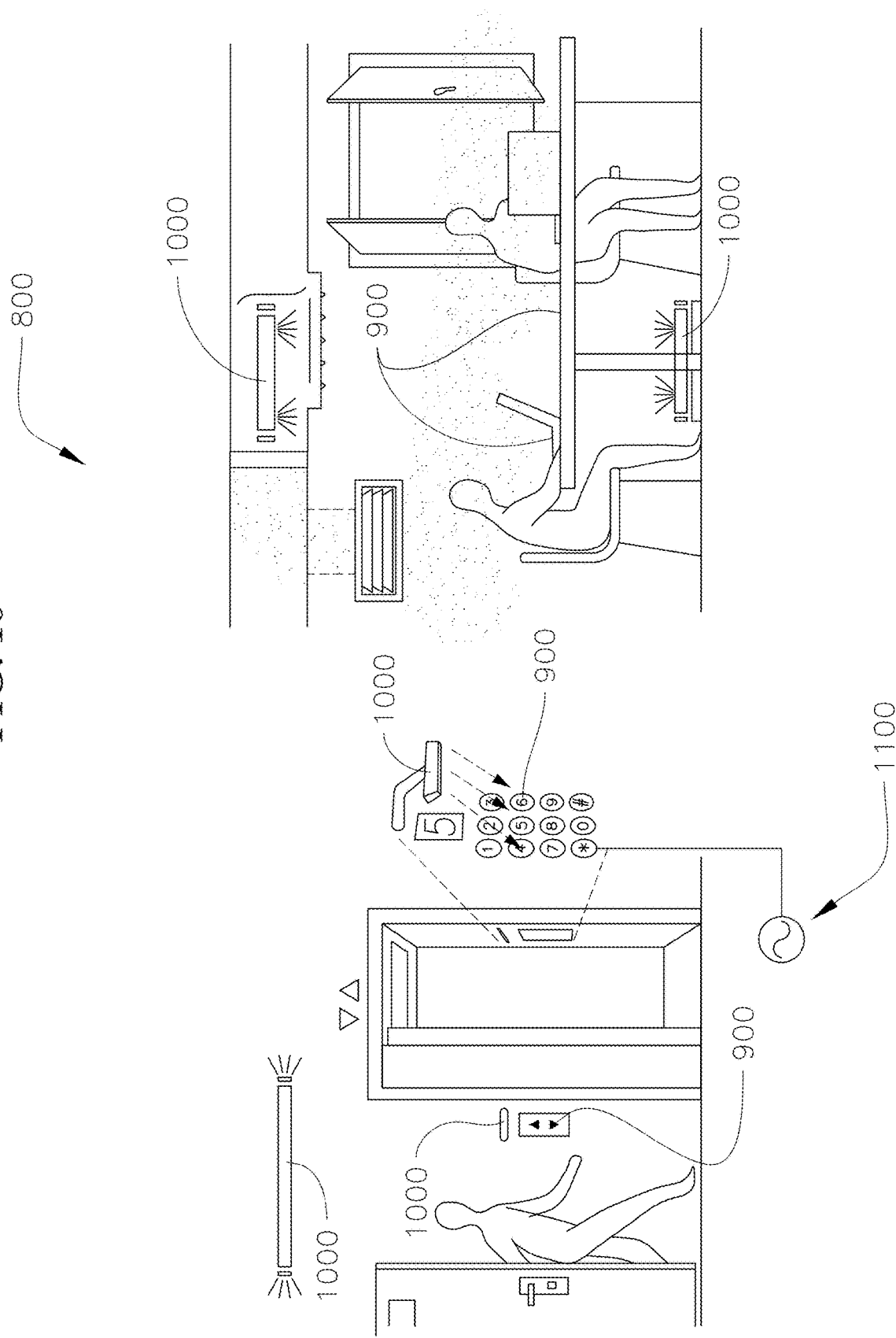
FIG. 10 is a sterilization system including a surface coating and a UV light source according to one embodiment of the present disclosure.

FIG. 10 depicts a sterilization system 800 according to one embodiment of the present disclosure including a surface coating 900 applied to an article or a fixture, and at least one UV light source 1000. The surface coating 900 may be the same as or similar to the embodiment of the surface coating 100 illustrated in FIGS. 1A-1B and/or the embodiment of the surface coating 500 illustrated in FIGS. 7A-7B. The surface coating 900 may be applied to any suitable article or fixture that is desired to be sterilized against microbial and viral pathogens (e.g., air-conditioning filtration systems, high-touch surfaces such as elevator buttons, doorknobs, and door handles, and/or any other surface that is likely to contribute to the transmission of pathogens). In one or more embodiments, the UV light source 1000 is configured (e.g., positioned and oriented) to irradiate the surface coating 900 with UV light (e.g., UVB and/or UVC light). In the illustrated embodiment, the UV light emitted from the UV light source 1000 may have a dosage safe for human exposure (e.g., UVC light having a dosage of approximately 3 mJ/cm$^2$ or less). As described above, the nano-antennae of the surface coating (e.g., the nano-antennae 104 of the surface coating 100 illustrated in FIGS. 1A-1B, or the nano-antennae 502 of the surface coating 500 illustrated in FIGS. 7A-7B) are configured to locally increase the electromagnetic field intensity at the dielectric gaps G from a dosage safe for human exposure to a level sufficient to kill the genetic material in the virus(es) and/or other microbial pathogens on the surface coating 900 (e.g., locally enhancing the electromagnetic field density at the dielectric gaps G by a factor of approximately 1,000 or more). Furthermore, in one or more embodiments, the sterilization system 800 may include a power source 1100 configured to supply an alternating current (AC) across the dielectric gaps G in the surface coating 900. Applying AC across the dielectric gaps G is configured draw and confine the virus(es) and/or other microbial pathogens on the surface coating 900 in the dielectric gaps G due to the phenomenon of dielectricphoresis (DEP). Drawing and confining the virus(es) and/or other microbial pathogens in the dielectric gaps G is configured to enable the UV light emitted from the one or more UV light sources 1000 to destroy viruses and/or other microbial pathogens located on portions of the surface coating 900 that do not enhance the dosage of the incident light (or that do not sufficiently enhance the dosage of the incident light) and that therefore might not otherwise be destroyed.

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims.

What is claimed is:

1. A surface coating configured to locally enhance ultraviolet light density of ultraviolet light incident on the surface coating, the surface coating comprising:
    a dielectric layer;
    a conductive layer on the dielectric layer;
    a plurality of nano-openings in the dielectric layer and the conductive layer;
    a plurality of nano-antennae in the plurality of nano-openings;
    a plurality of dielectric gaps between the plurality of nano-antennas and the conductive layer, wherein the conductive layer and the plurality of nano-antennae both comprise a UV plasmonic material; and
    an alternating current source applied to the plurality of nano-antennae and the conductive layer across the plurality of dielectric gaps.

2. The surface coating of claim 1, wherein each dielectric gap of the plurality of dielectric gaps has a distance of approximately 10 nm or less.

3. The surface coating of claim 1, wherein the UV plasmonic material is selected from the group of materials consisting of aluminum (Al), gallium (Ga), indium (In), tin (Sn), thallium (Tl), lead (Pb), bismuth (Bi), magnesium (Mg), germanium (Ge), gallium nitride (GaN), aluminum nitride (AlN), and combinations thereof.

4. The surface coating of claim 1, wherein the dielectric layer comprises polymethyl methacrylate (PMMA).

5. The surface coating of claim 1, wherein each nano-antenna of the plurality of nano-antennae has a shape selected from the group consisting of a circular shape, an elliptical shape, a square shape, a rectangular shape, and a tapered shape.

6. The surface coating of claim 5, wherein an average diameter of the plurality of nano-antennae is in a range from approximately 20 nm to approximately 500 nm.

7. The surface coating of claim 1, wherein at least one nano-antenna of the plurality of nano-antennae has a shape or size different than another nano-antenna of the plurality of nano-antennae.

8. The surface coating of claim 1, wherein a periodicity of the plurality of nano-antennae is in a range from approximately 50 nm to approximately 1,000 nm.

9. The surface coating of claim 1, the plurality of nano-openings and the plurality of nano-antennae are provided over at least 60% of the surface coating.

10. A method of manufacturing the surface coating of claim 1, the method comprising:
    depositing a mixture of a first polymer and a second polymer on a substrate, the second polymer self-arranging into a plurality of spots;
    selectively removing the plurality of spots to form the plurality of nano-openings in the dielectric layer formed by the first polymer;
    depositing a UV plasmonic material on the dielectric layer and in the plurality of nano-openings, the UV plasmonic material forming the plurality of nano-antennae in the plurality of nano-openings and the conductive layer on the dielectric layer.

11. The method of claim 10, wherein the depositing of the mixture comprises a process selected from the group consisting of brushing, spraying, dipping, vapor deposition, and printing.

12. The method of claim 10, wherein the depositing of the UV plasmonic material comprises e-beam evaporation or molecular beam deposition of the UV plasmonic material.

13. The method of claim 10, wherein the first polymer comprises polymethyl methacrylate (PMMA) and the second polymer comprises polystyrene (PS).

14. A surface coating configured to locally enhance ultraviolet light density, the surface coating comprising:
    a layer of UV plasmonic material comprising a plurality of nano-antennae;
    a dielectric pattern in the layer of UV plasmonic material, the dielectric pattern spacing adjacent nano-antennae of the plurality of nano-antennae apart from each other by a dielectric gap; and
    an alternating current source applied to the adjacent nano-antennae across the dielectric gap.

15. The surface coating of claim 14, wherein the dielectric gap has a distance of approximately 10 nm or less.

16. The surface coating of claim 14, wherein the UV plasmonic material is selected from the group of materials consisting of aluminum (Al), gallium (Ga), indium (In), tin (Sn), thallium (Tl), lead (Pb), bismuth (Bi), magnesium (Mg), germanium (Ge), gallium nitride (GaN), aluminum nitride (AlN), and combinations thereof.

17. The surface coating of claim 14, wherein the dielectric pattern has a pattern selected from the group of patterns consisting of an array of shapes, grid lines, stripes, chevrons, a sawtooth pattern, a crisscross pattern, and combinations thereof.

18. The surface coating of claim 14, wherein an average width of the plurality of nano-antennae is in a range from approximately 20 nm to approximately 500 nm.

19. A method of manufacturing the surface coating of claim 14, the method comprising:
    depositing a UV plasmonic material on a substrate to form a first plurality of projections on the substrate, the first plurality of projections being spaced apart from each other by spaces;
    depositing a dielectric material on the first plurality of projections and in the spaces between the first plurality of projections;
    depositing the UV plasmonic material to form a second plurality of projections in the spaces between the first plurality of projections and a plurality of excess projections on the first plurality of projections;
    removing the plurality of excess projections; and
    selectively removing portions of the dielectric material on the first plurality of projections, wherein the first plurality of projections and the second plurality of projections define the plurality of nano-antennae of the layer of UV plasmonic material, and wherein remaining portions of the dielectric material define the dielectric pattern.

20. The method of claim 19, wherein the removing of the plurality of excess projections comprises applying an adhesive on the plurality of excess projections, and peeling off the adhesive and the plurality of excess projections adhered thereto.

* * * * *